United States Patent [19]

Cooperman et al.

[11] Patent Number: 5,723,316
[45] Date of Patent: *Mar. 3, 1998

[54] α-1-ANTICHYMOTRYPSIN ANALOGUES HAVING CHYMASE INHIBITING ACTIVITY

[75] Inventors: Barry S. Cooperman, Penn Valley; Harvey Rubin, Philadelphia; Norman Schechter, Philadelphia; Zhi Mei Wang, Philadelphia, all of Pa.

[73] Assignee: Trustees of the University of Pennsylvania, Philadelphia, Pa.

[*] Notice: The term of this patent shall not extend beyond the expiration date of Pat. No. 5,613,194.

[21] Appl. No.: 221,171

[22] Filed: Mar. 31, 1994

Related U.S. Application Data

[63] Continuation-in-part of Ser. No. 221,078, Mar. 31, 1994, Ser. No. 5,898, Jan. 15, 1993, abandoned, and Ser. No. 5,908, Jan. 15, 1993, Pat. No. 5,367,064, said Ser. No. 5,898, and Ser. No. 5,908, each is a division of Ser. No.735,322, Jul. 24, 1991, Pat. No. 5,266,465, which is a division of Ser. No. 370,704, Jun. 23, 1989, Pat. No. 5,079,336, said Ser. No. 221,078, is a continuation-in-part of Ser. No. 5,898, and Ser. No. 5,908.

[51] Int. Cl.$^6$ .............. C12N 15/00; C12N 5/10; A61K 38/43
[52] U.S. Cl. ............ 435/69.2; 435/172.3; 435/240.2; 435/252.3; 514/12; 530/350; 530/395; 536/23.5
[58] Field of Search ............... 435/69.2, 172.3, 435/320.1, 240.2, 252.3; 514/12; 530/350, 395; 536/23.5

[56] References Cited

U.S. PATENT DOCUMENTS

| | | | |
|---|---|---|---|
| 4,732,973 | 3/1988 | Barr et al. | 530/350 |
| 4,916,117 | 4/1990 | Lezdey et al. | 514/8 |
| 5,008,242 | 4/1991 | Lezdey et al. | 514/8 |
| 5,079,336 | 1/1992 | Rubin et al. | 530/350 |
| 5,252,725 | 10/1993 | Rubin et al. | 536/23.5 |
| 5,266,465 | 11/1993 | Rubin et al. | 435/69.2 |

OTHER PUBLICATIONS

Ardelt and Laskowski, Turkey Ovomucoid Third Domain Inhibits Eight Different Serine Prtoeinases of Varied Specificity on the Same . . . Leu$^{18}$–Glu$^{19}$ . . . Reactive Site *Biochemistry*, 1985, 24, 5313.

Bainton, et al., Differences in Enzyme content of Azurophil and Specfic Granules of Polymorphonuclear Leukocytes *J. Cell Biol*, 1968, 39, 286.

Bainton, et al., Differences in Enzyme Content of Axurophil and Specific Grnaules of Polymorphonulcear Leukocytes *J. Cell. Biol.*, 1968, 39, 299.

Cooperman et al. Antichymotrypsin Interaction with Chymotrypsin *J. Biol. Chem.* 1993 268:23616–23625.

Baird et al., *Physiol.*, 1986, 61, 2224.

Beatty et al. Kinetics of Association of Serine Proteinases with Native and Oxidized α–1–Proteinase Inhibitor and α–1–Antichymotrypsin *J. Biol. Chem.* 1980.

Campbell, et al., Proteolysis bt Neutrophils; Relative importance of cell–substrate contact and oxidative inactivation of proteinase inhibitors in vitro *J. Clin. Invest.*, 1982, 70, 845.

Camussi, G. et al., Synthesis and Release of Platelet–Activating Factor is Inhibited by Plasma α1–Proteinase Inhibitor or α1–Antichymotrypsin and is stimulated by Proteinases *J. Exp. Med.*, 1988, 168, 1293.

Carrell et al. Plakalbumin, $\alpha_1$–antitrypsin, antithrombin and the mechanism of inflammatory thrombosis *Nature* 1985 317:730–732.

Camussi, G. et al., Tumor Necrosis Factor Stimulates human neutrophils to release leukotriene $B_4$ and platelet–activating factor *Eur. J. Biochem.*, 1989, 182, 661.

Chandra et al. Sequence Homology between Human α1–Antichymotrypsin, α1–Antitrypsin, and Antithrombin III *Biochemistry* 1983 22:5055–5060.

Petersen and Clemmensen, Kinetics of Plasmin Inhibition in the Presence of a Synthetic Tripeptide substrate *Biochem. J.*, 1981, 199, 121.

Redens et al., Synergistic Protection from Lung Damage by Combining Antithrombin–III and Alpha1–Proteinase Inhibitor in the *E. coli* Endotoxemic Sheep Pulmonary Dysfunction Model *Circ. Shock*, 1988, 26, 15.

Rosengren et al., Neutrophil–mediated vascular leakage is not suppressed by leukocyte elastase inhibitors *Am. J. Physiol.*, 1990, 259, H1288.

Potempa, et al., Proteolytic Inactivation of α–1–Anti–chymotrypsin sites of cleavage and generation of chemotactic activity *J. Biol. Chem.*, 1991, 266, 21482.

DelMar et al., A Sensitive New Substrate for Chymotrypsin *Anal. Biochem.* 1979, 99, 316.

Emerson et al., Protection Against Disseminated Intravascular Coagulation and Death by Antithrombin–III in the *Escherichis coli* Endotexemic Rat *Circ. Shock*, 1987, 21, 1.

(List continued on next page.)

*Primary Examiner*—Stephen Walsh
*Assistant Examiner*—David S. Romeo
*Attorney, Agent, or Firm*—Law Offices of Jane Massey Licata

[57] ABSTRACT

The invention provides analogues of α-1-antichymotrypsin having amino acid substitutions at position 358. α-1-antichymotrypsin analogues having amino acid substitutions at positions 356–361 and analogues having amino acid substitutions at positions 356–361 wherein the amino acid at position 358 is substituted are also within the scope of the invention. These analogues exhibit chymase inhibitory activity. Also provided are novel α-1-antichymotrypsins having an N-terminal extension of methionine-alanine-serine or alanine-serine. Expression vectors for the production of α-1-antichymotrypsins are also provided. The present invention also provides host cells and cell cultures capable of expressing analogues of α-1-antichymotrypsin, as well as protein preparations from the host cells. Methods of producing and using the analogues of α-1-antichymotrypsin to inhibit chymase activity are also provided.

31 Claims, 6 Drawing Sheets

OTHER PUBLICATIONS

Hill et al. Plasma Protease Inhibitors in mouse and man *Nature* 1984 311:175–177.

Nagai et al., Administration of $\alpha_1$-Proteinase Inhibitor Ameliorates Bleomycin–induced Pulmnary Fibrosis in Hamsters *Am. Rev. Resp. Dis.*, 1992, 145, 651.

Kilpatrick et al., Inhibition of Human Neutrophil Superoxide Generation by ®1–Antichymotrypsin *J. Immunol.*, 1991, 146, 2388.

Laemmli, U.K. Cleavage of Structural Proteins during the Assembly of the Head of Bacteriophage T4 *Nature (London)* 1970 227:680–685.

Maniatis et al. Molecular Cloning: A Laboratory Manual, Cold Spring Harbor Laboratory Press, Cold Spring Harbor, New York, 1982 249–255.

Morii et al. Amino Acid Sequence at the Reactive Site of Human $\alpha_1$–Antichymotrypsin *J. Biol. Chem.* 1983 258:12749–12752.

Nathan, Neutrophil Activation on Biological Surfaces *J. Clin Invest.*, 1980, 80, 1550.

Renesto, P. et al., Tumor Necrosis Factor–$\alpha$ Enhances Platelet Activation Via Cathepsin G Released From Neutrophils *J. Immunol.*, 1991, 146, 2305.

Sambrook et al., *Molecular Cloning: A Laboratory Manual*, second edition, Cold Spring Harbor Laboratory Press, Cold Spring Harbor, NY (1989).

Sanger et al., DNA sequencing with chain–terminating inhibitors *Proc. Nat'l. Acad. Sci, U.S.A.*, 1977, 74, 5463.

Schechter et al. Reaction of Human Chymase With Reactive Site Variants of $\alpha$1–Antichymotrypsin *J. Biol. Chem.* 1993 268:23626–23633.

Schonbaum et al., The Spectrophotometric Determination of the Operational Normality of an $\alpha$–Chymotrypsin Solution *J. Biol. Chem.*, 1961, 236, 2930.

Studier and Moffatt, Use of Bacteriophage T7 RNA Polymerase to Direct Selective High–leve Expression of Cloned Genes *J. Mol. Biol.*, 1986, 189, 113.

Towbin et al. Electrophoretic transfer of proteins from polyacrylamide gels to nitrocellulose sheets *Proc. Nat'l Acad. Sci. USA* 1979 76:4350–4354.

Travis and Fritz, Potential Problems in Designing Elastase Inhibitors for Therapy *Am. Rev. Resp. Dis.* 1991, 43, 1412.

Tsuda et al.,Purification, Properties and Identification of A Serum DNA Binding Protein and Its Microheterogeneity *J. Exp. Clin. Med.*, 1982, 7, 201.

Wachter et al. Cloning A Serine Protease Inhibitor Gene With An Antibody Specific Probe Abstract, Jan. 1987, American Academy of Allergy and Immunology.

Wachter et al. Cloning an Antigenic Determinants of Serine Protease Inhibitors Abstract, Jan. 1987, 43 Annual Meeting, Annals of Allergy.

Weiss, et al., Neutrophil–Mediated Solubilization of the Subendothelial Matrix: Oxidative and nonoxidative mechanisms of proteolysis used by normal and chronic granulomatous disease phagcytes *J. Immunol.*, 1986, 136, 636.

Young and Davis, Efficient isolation of genes by using antibody probes *Proc. Natl. Acad. Sci., U.S.A.*, 1977, 74, 5463.

Young et al. Efficient isolation of genes by using antibody probes *Proc. Natl. Acad. Sci. USA* 1983 80:1194–1198.

Rubin et al. Cloning, Expression, Purification, and Biological Activity of Recombinant Native and Variant Human $\alpha$1–Antichymotrypsins *J. Biol. Chem.* 1990 265:1199–1207.

Jallat et al. Prot. Eng. 1986 1:29–35.

Kilpatrick et al. Native and Recombinant $\alpha$–1 Antichymotrypsin (ACT) Inhibit Superoxide Anion ($O_2-$) Generation in Human Neutrophils Society for Leukocyte Biology Marco Island, F1 1989.

Schoenberger et al. Limited proteolysis of C1–inhibitor by chymotrypsin–like proteinases *FEBS Letters* 1989 259:165–167.

Schechter et al. On The Size of The Active Site In Proteases *Biochem. and Biophy. Res. Comm.* 1967 27:157–162.

Nakajima et al. Mapping the Extended Substrate Binding Site of Cathepsin G and Human Leukocyte Elastase *J. Biol. Chem.* 1979 254:4027–4032.

Meister et al. Immunohistochemical Characterization of Hitiocytic Tumours *Diagnostic Histopathology* 1981 4:79–87.

Rubin H. The Biology and Biochemistry of Antichymotrypsin and its Potential Role as a Therapeutic Agent *Biol Chem* 1992 373:497.

Wei et al. Crystallization, Activity Assay and preliminary X–ray Diffraction Analysis of the Uncleaved Form of the Serpin Antichymotrypsin *J. Mol. Biol.* 1992 226:273–276.

```
CTC TGC CAC CCT AAC AGC CCA CTT GAC GAG GAG AAT CTG ACC CAG GAG AAC CAA
Leu Cys His Pro Asn Ser Pro Leu Asp Glu Glu Asn Leu Thr Gln Glu Asn Gln
                10              20              30              40              50

GAC CGA GGG ACA CAC GTG GAC CTC GGA TTA GCC TCC GCC AAC GTG GAC TTC GCT
Asp Arg Gly Thr His Val Asp Leu Gly Leu Ala Ser Ala Asn Val Asp Phe Ala
        60              70              80              90             100

TTC AGC CTG TAC AAG CAG TTA GTC CTG AAG GCC CCT GAT AAG AAT GTC ATC TTC
Phe Ser Leu Tyr Lys Gln Leu Val Leu Lys Ala Pro Asp Lys Asn Val Ile Phe
       110             120             130             140             150             160

TCC CCA AGC ATC TCC ACC GCC TTG GCC TTC CTG TCT CTG GGG GCC CAT AAT
Ser Pro Ser Ile Ser Thr Ala Leu Ala Phe Leu Ser Leu Gly Ala His Asn
       170             180             190             200             210

ACC ACC CTG ACA GAG ATT CTC AAA GGC TTG AAG TTC AAC CTC ACG GAG ACT TCT
Thr Thr Leu Thr Glu Ile Leu Lys Gly Leu Lys Phe Asn Leu Thr Glu Thr Ser
       220             230             240             250             260             270

GAG GCA GAA ATT CAC CAG AGC TTC CAG CAC CTC CTG CGC ACC CTC AAT CAG TCC
Glu Ala Glu Ile His Gln Ser Phe Gln His Leu Leu Arg Thr Leu Asn Gln Ser
       280             290             300             310             320
```

Fig. 1a

```
330
AGC GAT GAG CTG CAG CTG AGT ATG GGA AAT GCC ATG TTT GTC AAA GAG CAA CTC
Ser Asp Glu Leu Gln Leu Ser MET Gly Asn Ala MET Phe Val Lys Glu Gln Leu 380                                                                   430
AGT CTG CTG GAC TTC ACG GAG GAT GCC AAG AGG CTG TAT GGC TCC GAG GCC
Ser Leu Leu Asp Arg Phe Thr Glu Asp Ala Lys Arg Leu Tyr Gly Ser Glu Ala

TTT GCC ACT GAC TTT CAG GAC TCA GCT GCA GCT AAG AAG CTC ATC AAC GAC TAC
Phe Ala Thr Asp Phe Gln Asp Ser Ala Ala Ala Lys Lys Leu Ile Asn Asp Tyr 490                                                                   540
GTG AAG AAT GGA ACT AGG GGG AAA ATC ACA GAT CTG ATC AAG GAC CTT GAC TCG
Val Lys Asn Gly Thr Arg Gly Lys Ile Thr Asp Leu Ile Lys Asp Leu Asp Ser

CAG ACA ATG ATG GTC CTG GTG AAT TAC ATC TTC TTT AAA GCC AAA TGG GAG ATG
Gln Thr MET MET Val Leu Val Asn Tyr Ile Phe Phe Lys Ala Lys Trp Glu MET 600                                                                   640
CCC TTT GAC CCC CAA GAT ACT CAT CAG TCA AGG TTC TAC TTG AGC AAA AAG AAG
Pro Phe Asp Pro Gln Asp Thr His Gln Ser Arg Phe Tyr Leu Ser Lys Lys Lys
```

Fig. 1b

```
         650                660              670              680                690            700
          |                  |                |                |                  |              |
TGG GTA ATG GTG CCC ATG ATG AGT TTG CAT CAC CTG ACT ATA CCT TAC TTC CGG
Trp Val MET Val Pro MET MET Ser Leu His His Leu Thr Ile Pro Tyr Phe Arg 710              720              730              740            750
                                |                |                |                |              |
GAC GAG GAG CTG TCC TGC ACC GTG GTG GAG CTG AAG TAC ACA GGC AAT GCC AGC
Asp Glu Glu Leu Ser Cys Thr Val Val Glu Leu Lys Tyr Thr Gly Asn Ala Ser 760                770              780              790                800            810
          |                  |                |                |                  |              |
GCA CTC TTC ATC CTC CCT GAT CAA GAC AAG ATG GAG GAA GTG GAA GCC ATG CTG
Ala Leu Phe Ile Leu Pro Asp Gln Asp Lys MET Glu Glu Val Glu Ala MET Leu 820              830              840              850            860
                                |                |                |                |              |
CTC CCA GAG ACC CTG AAG CGG TGG AGA GAC TCT CTG GAG TTC AGA GAG ATA GGT
Leu Pro Glu Thr Leu Lys Arg Trp Arg Asp Ser Leu Glu Phe Arg Glu Ile Gly 870                880              890              900                910
          |                  |                |                |                  |
GAG CTC TAC CTG CCA AAG TTT TCC ATC TCG AGG GAC TAT AAC CTG AAC GAC ATA
Glu Leu Tyr Leu Pro Lys Phe Ser Ile Ser Arg Asp Tyr Asn Leu Asn Asp Ile 920              930              940              950            960              970
                                |                |                |                |              |                |
CTT CTC CAG CTG GGC ATT GAG GAA GCC TTC ACC AGC AAG GCT GAC CTG TCA GGG
Leu Leu Gln Leu Gly Ile Glu Glu Ala Phe Thr Ser Lys Ala Asp Leu Ser Gly
```

*Fig. 1c*

```
     980            990          1000          1010          1020
      |              |             |             |             |
ATC ACA GGG GCC AGG AAC CTA GCA GTC GAA GCA TCT GCC ACA GCA GTC AAA ATC ACC
Ile Thr Gly Ala Arg Asn Leu Ala Val Glu Ala Ser Ala Thr Ala Val Lys Ile Thr 1030          1040          1050          1060          1070          1080
    |             |             |             |             |             |
GAT GTA TTT GAG GAG GGC ACA GAA GCA TCT GCC ACA GCA GTC AAA ATC ACC
Asp Val Phe Glu Glu Gly Thr Glu Ala Ser Ala Thr Ala Val Lys Ile Thr
                                    349 350

1090          1100          1110          1120          1130
    |             |             |             |             |
CTC CTT TCT GCA TTA GTG GAG ACA AGG ACC ATT GTG CGT TTC AAC AGG CCC TTC
Leu Leu Ser Ala Leu Val Glu Thr Arg Thr Ile Val Arg Phe Asn Arg Pro Phe
 P₁  P₁' P₁'                                   368 369

1140          1150          1160          1170          1180
    |             |             |             |             |
CTG ATG ATC ATT GTC CCT ACA GAC ACC CAG AAC ATC TTC TTC ATG AGC AAA GTC
Leu MET Ile Ile Val Pro Thr Asp Thr Gln Asn Ile Phe Phe MET Ser Lys Val 1190          1200          1210          1220          1230          1240
    |             |             |             |             |             |
ACC AAT CCC AAG CAA GCC TAG AGC TTG CCA TCA AGC AGT GGG GCT CTC AGT AAG
Thr Asn Pro Lys Gln Ala ---  Ser Leu Pro Ser Ser Ser Gly Ala Leu Ser Lys
```

*Fig. 1d*

```
1250                    1260                    1270                    1280                    1290
 —|                      —|                      —|                      —|                      —|
GAA CTT GGA ATG CAA GCT GGA TGC CTG GGT CTC TGG CAC AGC CTG GCC CCT GTG
Glu Leu Gly MET Gln Ala Gly Cys Leu Gly Leu Trp His Ser Leu Ala Pro Val 1300                    1310                    1320                    1330                    1340                    1350
 —|                      —|                      —|                      —|                      —|                      —|
CAC CGA GTG GCC ATG GCA TGT GTG GCC CTG TCT GCT TAT CCT TGG AAG GTG ACA
His Arg Val Ala MET Ala Cys Val Ala Leu Ser Ala Tyr Pro Trp Lys Val Thr 1360                    1370                    1380                    1390                    1400
 —|                      —|                      —|                      —|                      —|
GCG ATT CCC TGT GTA GCT CTC ACA TGC ACA GGG GCC CAT GGA CTC TTC AGT CTG
Ala Ile Pro Cys Val Ala Leu Thr Cys Thr Gly Ala His Gly Leu Phe Ser Leu 1410        1420
 —|          —|
GAG GGT CCT GGG CCT CCT GGA ATT
Glu Gly Pro Gly Pro Pro Gly Ile
```

*Fig. 1e*

α-1-ANTICHYMOTRYPSIN ANALOGUES HAVING CHYMASE INHIBITING ACTIVITY

REFERENCE TO RELATED APPLICATIONS

The present application is a continuation-in-part of U.S. patent application Ser. No. 08/221,078, filed concurrently herewith on Mar. 31, 1994, the concurrently filed applications are continuations-in-part of U.S. patent application Ser. No. 08/005,898, now abandoned, and U.S. patent application Ser. No. 08/005,908, both filed Jan. 15, 1993, now U.S. Pat. No. 5,367,064, which are divisionals of U.S. patent application Ser. No. 07/735,322, filed Jul. 24, 1991, now U.S. Pat. No. 5,266,465, which is in turn a divisional application of U.S. patent application Ser. No. 07/370,704 filed Jun. 23, 1989, which is now U.S. Pat. No. 5,079,336. The disclosures of each of these applications is hereby incorporated by reference.

REFERENCE TO GOVERNMENT GRANTS

The work for the present invention was supported in part by National Institutes of Health grants AG-10599 and AR-39674. The United States government may have certain rights in the invention.

FIELD OF THE INVENTION

This invention is related to the field of substances produced by recombinant DNA technology and more particularly to the field of proteins produced by recombinant DNA technology.

BACKGROUND OF THE INVENTION

The interaction of serine protease inhibitors, serpins (serpin—serine proteinase inhibitor), with endogenous and microbial proteases produces a spectrum of molecular species each of which are components of a highly evolutionarily conserved homeostatic mechanism that operates to maintain a concentration of intact, active serpins pivotal in host survival. Of these species, the serpin-enzyme complex and the hydrolyzed, inactive form of the intact serpin stimulate the production of IL-6, signaling hepatocytes to increase synthesis of the acute phase proteins including a subpopulation of the serpin superfamily of proteins. Although serpin-enzyme complexes are rapidly cleared from the circulation, they may accumulate along with the cleaved and intact forms in local areas of inflammation. This establishes a complex microenvironment of chemoattractants and inhibitors of chemotaxis as well as activators and inhibitors of neutrophil degranulation, leukotriene, platelet activating factor (PAF) and superoxide production. Kilpatrick et al. have shown that native antichymotrypsin (ACT) and recombinant antichymotrypsin (rACT) inhibited superoxide generation by human neutrophils in suspension. Kilpatrick et al., *J. Immunol.*, 1991, 146, 2388. In this system, intact ACT and rACT complexed with chymotrypsin (Chtr) were equally effective in inhibiting free radical production by neutrophils stimulated with f-Met-Leu-Phe, Concanavalin A (ConA) or phorbol myristate acetate (PMA).

A variety of animal models corroborate the hypothesis that runaway serine protease activity is a major mechanism of lung injury and that an appropriate serpin response controls the degree of the injury. For example, antithrombin III (ATIII) in combination with alpha-1-protease inhibitor (α1PI), protected sheep from endotoxin-induced lung injury where the individual serpins were not as effective as the combination. Redens et al., *Circ. Shock*, 1988, 26, 15. Redens et al. also showed that ATIII protects against the development of disseminated intravascular coagulation in endotoxemic rats. Emerson et al., *Circ. Shock*, 1987, 21, 1. A scavenger of $H_2O_2$ and a chloromethyl ketone inhibitor of elastase blocked reactive oxygen potentiation of neutrophil elastase-mediated acute edematous lung injury in a rat and α1PI diminished bleomycin-mediated pulmonary inflammation as well as subsequent fibrosis. Baird et al., *Physiol.*, 1986, 61, 2224 and Nagai et al., *Am. Rev. Resp. Dis.*, 1992, 145, 651. While in another system, however, neutrophil elastase inhibitors, Eglin C and a low molecular weight compound L 658,758, failed to inhibit leukotriene B4 (LTB4)-induced neutrophil-mediated adherence, diapedesis or vascular leakage. Rosengren et al., *Am. J. Physiol.*, 1990, 259, H1288.

Accordingly, inhibitors of proteolytic enzymes administered therapeutically may limit the molecular and cellular mechanisms of inflammation and reduce tissue damage. Therefore, there remains a need for safe and effective inhibitors such as α-1-antichymotrypsin for clinical applications in animals. Therapeutic agents based on multifunctional protease inhibitors will clinically advance therapy of diseases where free radicals as well as proteases have been implicated in the mechanism of injury such as the adult respiratory syndrome, pancreatitis, inflammatory skin lesions and reperfusion injury.

SUMMARY OF THE INVENTION

The present invention provides analogues of human α-1-antichymotrypsin having antichymotrypsin activity and/or chymase inhibitory activity. The present invention includes α-1-antichymotrypsin analogues having an amino acid substitution at position 358 such that the wild type position 358, leucine, is changed to an amino acid selected from tryptophan, alanine, asparagine, aspartic acid, cysteine, glutamine, glutamic acid, glycine, histidine, isoleucine, lysine, methionine, phenylalanine, proline, serine, threonine, tyrosine, and valine. Also included in the scope of the present invention is an analogue of human α-1-antichymotrypsin wherein the amino acids corresponding to the amino acids Thr-Leu-Leu-Ser-Ala-Leu (SEQ ID NO: 7) at positions 356 to 361 of wild-type α-1-antichymotrypsin are substituted with amino acids Ile-Pro-Xxx-Ser-Ile-Pro (SEQ ID NO: 8). SEQ ID NO: 8 may also be substituted at position 358 with an amino acid selected from the group set forth above.

The novel polypeptides indicated above, as well as human wild type α-1-antichymotrypsin, FIG. 1, may have an N-terminal extension sequence of methionine-alanine-serine or alanine-serine. The novel polypeptides having an N-terminal extension are produced from the nucleotide sequence encoding the entire amino acid sequence of mature human wild type α-1-antichymotrypsin, optionally having one of the substitutions indicated above, with an N-terminal extension sequence of methionine-alanine-serine or alanine-serine.

These novel α-1-antichymotrypsin analogues result in stable α-1-antichymotrypsin monomers and eliminates an N-terminal cysteine present in the rACT described precursor α-1-antichymotrypsin polypeptide that gave rise to protein dimers and apparent heterogeneity. These α-1-antichymotrypsin polypeptides have antichymotrypsin activity and are useful in the same manner as α-1-antichymotrypsin itself. The analogues of the present invention are also useful for chymase inhibition.

The present invention also provides expression vectors comprising nucleic acid sequences coding for the α-1- antichymotrypsin analogues of the invention, transformed host cells and cell cultures capable of expressing the analogues of the invention. The present invention further provides methods of producing α-1-antichymotrypsin analogues comprising culturing a host cell capable of expressing α-1-antichymotrypsin analogues.

The present invention also provides methods of inhibiting chymase comprising contacting chymase with an inhibitory amount of at least one α-1-antichymotrypsin analogue. A method of using α-1-antichymotrypsin analogues to inhibit chymase activity comprising adding an effective amount of an α-1-antichymotrypsin analogue of the invention to a sample exhibiting chymase activity is also provided.

The scope of the present invention provides analogues of human wild type α-1-antichymotrypsin which are useful in the treatment of lung inflammation, reperfusion injury, and treating and preventing blood clots. Medicaments and compositions comprising analogues of human wild type α-1-antichymotrypsin in pharmaceutically acceptable amounts together with a carrier are also the subject of the present invention, as are their uses in treating the conditions identified above.

This invention is more particularly pointed out in the appended claims and is described in its preferred embodiments in the following description.

BRIEF DESCRIPTION OF THE FIGURES

FIGS. 1a–e show the complete nucleotide sequence and predicted amino acid sequence of human wild type α-1-antichymotrypsin. The full length gene is encoded by nucleotide residues 1–1209.

DETAILED DESCRIPTION OF THE INVENTION

Figure 2:
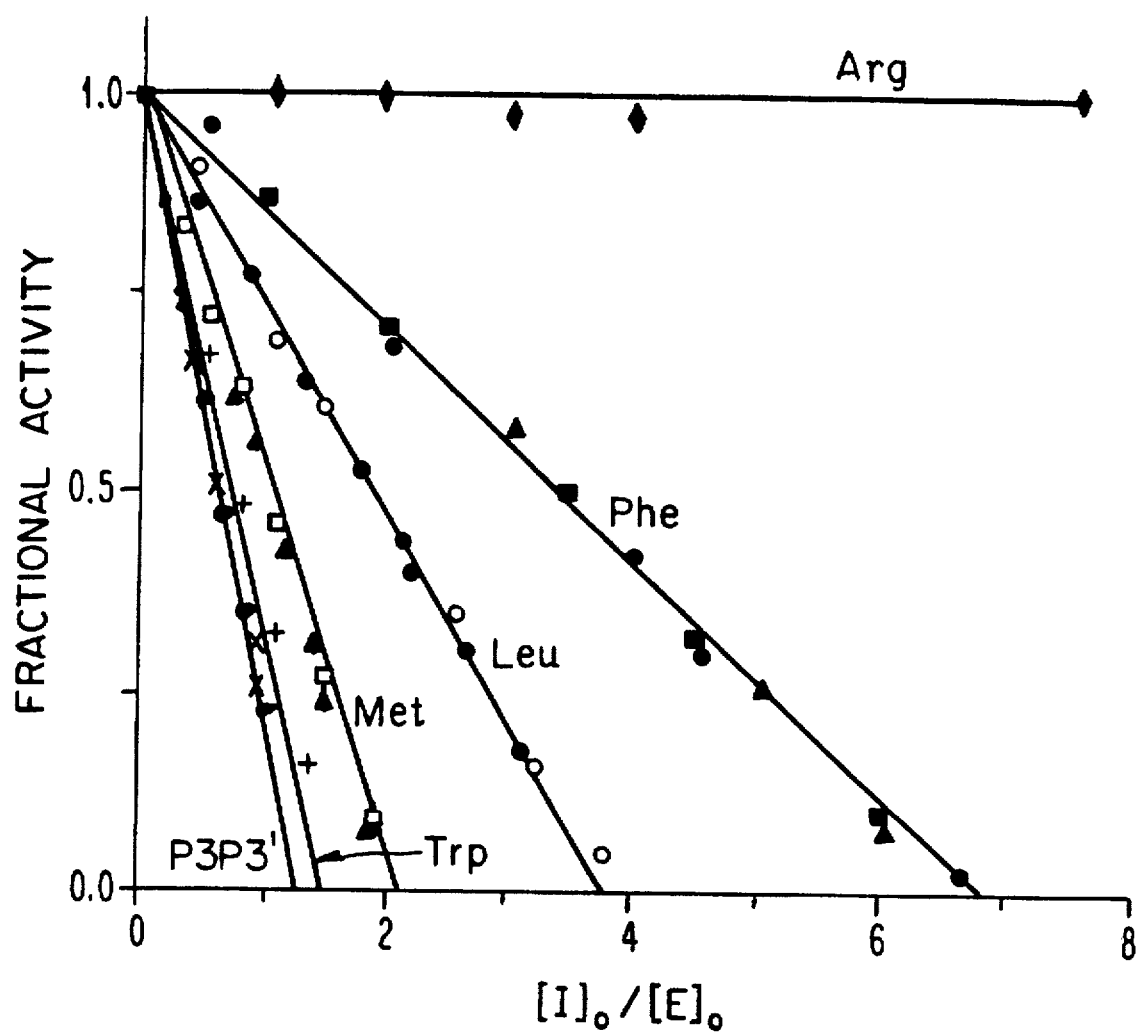
FIG. 2 is a graph of the titration of human chymase with α-1-antichymotrypsin analogues.

The present invention provides analogues of human α-1-antichymotrypsin wherein the amino acid corresponding to leucine at amino acid position 358 of wild type human α-1-antichymotrypsin is substituted with an amino acid selected from tryptophan, alanine, asparagine, aspartic acid, cysteine, glutamine, glutamic acid, glycine, histidine, isoleucine, lysine, methionine, phenylalanine, proline, serine, threonine, tyrosine, and valine. In a preferred embodiment of the invention, leucine at position 358 is substituted with tryptophan.

An analogue of α-1-antichymotrypsin wherein amino acids Thr-Leu-Leu-Ser-Ala-Leu (SEQ ID NO: 7) at positions 356–361 are substituted with Ile-Pro-Xxx-Ser-Ile-Pro (SEQ ID NO: 8) is also provided by the present invention. The analogues having amino acid substitutions at positions 356–361 may be substituted at position 358 with an amino acid selected from the group consisting of methionine, tryptophan, alanine, asparagine, aspartic acid, cysteine, glutamine, glutamic acid, glycine, histidine, isoleucine, lysine, phenylalanine, proline, serine, threonine, tyrosine, and valine.

Wild type antichymotrypsin having alterations in the amino acid leucine at position 358 results in analogues referred to as rACT-L358 followed by the one letter amino acid symbol substituted in a particular analogue. For example, rACT-L358W represents recombinant α-1-antichymotrypsin having tryptophan at amino acid position 358.

Another aspect of the invention provides human α-1-antichymotrypsin, in wild type and analogue forms, having an N-terminal extension of Met-Ala-Ser. In this embodiment of the invention, mature human α-1-antichymotrypsin contains three additional amino acids at the N-terminus, Met-Ala-Ser. Another embodiment comprises mature human α-1-antichymotrypsin, in wild type and analogue forms, with Met cleaved and two amino acids, Ala-Ser, remaining at the N-terminus. Wild type and analogue forms of α-1-antichymotrypsin may have the N terminal extensions disclosed herein.

α-1-Antichymotrypsin is a serine protease inhibitor (serpin). In its native, circulating form, it is a glycoprotein of between 55,000 and 66,000 daltons, with the variation attributed to microheterogeneity in glycosylation. It is synthesized predominantly in the liver and has also been reported in mast cells, sinus histiocytes, endothelial cells and in cells of the histio/monocytic line. In response to inflammatory stimuli, plasma levels of α-1-antichymotrypsin increase more than four-fold within several hours.

Chymotrypsin-like enzymes and their inhibitors have been identified in a wide variety of normal and abnormal biological processes including modulation of cellular functions, DNA-binding, inhibition of certain parasite functions and processing of vasoconstrictor proteins. In addition, α-1-antichymotrypsin appears to be a component of the amyloid deposit in Alzheimer's plaques and is present in various carcinomas and in some tissues of the reproductive system.

Human α-1-antichymotrypsin forms sodium dodecyl sulfate (SDS)-stable complexes with its target enzymes, which is a general property of serpin/serine protease interactions. Very little is known about the nature of these complexes. Although high-resolution crystal structures of chymotrypsin and chymotrypsin/small molecular inhibitor complexes have been resolved and NMR analyses of the enzyme have been reported, no direct structural studies of human α-1-antichymotrypsin alone or as a complex with a serine protease have been reported.

There is evidence that proteases and oxidants play a central role in establishing and maintaining shock physiology and that protease inhibitors can favorably modify the outcome of shock. Small molecule protease inhibitors have been shown to have efficacy in pancreatitis in humans. Similarly, antichymotrypsins may be implicated in treatment of coagulation disorders as in liver diseases. Proteases are also important mediators of inflammatory diseases. Regulation of these enzymes by their inhibitors is critical for the control of tissue destruction in these diseases.

The analogues of the invention, having an amino acid substitution at amino acid position 358, the analogues having amino acids substitutions at amino acid positions 356–361 of wild-type α-1-antichymotrypsin with position 358 having an amino acid selected from the amino acids set forth above, are surprisingly and unexpectedly much better inhibitors of chymase, a proteinase stored at high concentrations within human mast cells, than wild-type or native antichymotrypsin. Human chymase is inhibited by two human serpin plasma inhibitors, α-1-antichymotrypsin and α-1-proteinase inhibitor. Both of these inhibitors are members of the serpin protein family. Although inhibition of chymase appeared irreversible with α-1-antichymotrypsin and α-1-proteinase inhibitor, showing the typical tight-binding complex resistant to denaturation in SDS, reactions with both inhibitors were not highly efficient. Determined under pseudo first order conditions, second order rate constants of 25,000 and 8,000 $M^{-1}S^{-1}$ were obtained for α-1-antichymotrypsin and α-1-proteinase inhibitor, respectively.

These values are approximately 100 to 1,000 fold lower than the values observed for the inhibition of neutrophil cathepsin G by α-1-antichymotrypsin, or the inhibition of neutrophil elastase by α-1-proteinase inhibitor. The inefficiency of the reaction was even more evident in titrations where endpoints yielded stoichiometries of inhibition (SI) of 4.5 (α-1-antichymotrypsin) and 5.0 (α-1-proteinase inhibitor) moles of inhibitor/mole of chymase. Analysis of these reactions by SDS-PAGE and by N-terminal sequence analysis of products indicated that the high stoichiometries of inhibition were due to a competing reaction producing a degraded inhibitor by hydrolysis within the reactive loop of the inhibitor.

The α-1-antichymotrypsin analogue wherein the leucine at position 358 of wild-type α-1-antichymotrypsin is substituted with tryptophan is a much more efficient inhibitor of chymase than the natural inhibitors. The stoichiometry of inhibition of approximately 1 mole of inhibitor/mole of chymase. Thus, the competing cleavage reaction is nearly eliminated, indicating that the analogues of the invention are four-fold more efficient for inhibition of chymase than wild type α-1-antichymotrypsin. The apparent second order rate constant for inhibition is more than five-fold greater than the apparent second order rate constant for inhibition of chymase by wild type α-1-antichymotrypsin, rACT, demonstrating a faster interaction.

Another aspect of the present invention provides nucleic acid sequences coding for α-1-antichymotrypsin and analogues, expression vectors and host cells transformed to express the nucleic acid sequences of the invention, protein preparations comprising the proteins of the present invention synthesized in a host cell transformed with a DNA sequence encoding the protein and cell cultures capable of expressing the nucleic acid sequence of the invention.

Generally, α-1-antichymotrypsin analogues, having amino acid substitutions at amino acid position 358 or having amino acid substitutions at amino acid positions 356–361 in the wild-type α-1-antichymotrypsin with position 358 having an amino acid selected from the amino acids identified above, are produced in host cells that have been transformed with an expression vector comprising a nucleic acid sequence coding for the particular protein. The host cells are cultured under conditions whereby the nucleic acid sequence coding for the particular protein is expressed. After a suitable amount of time for the protein to accumulate, the protein is purified from the host cells or medium surrounding the cells.

A human gene coding for α-1-antichymotrypsin can be readily obtained from a human liver cDNA library. Suitable libraries can be obtained from commercial sources such as Clontech, Palo Alto, Calif. Positive clones are then subjected to DNA sequencing to determine the presence of a DNA sequence coding for α-1-antichymotrypsin. DNA sequencing is readily accomplished using the chain termination method of Sanger et al., *Proc. Nat'l. Acad. Sci, U.S.A.*, 1977, 74, 5463.

The DNA sequence coding for α-1-antichymotrypsin may then be manipulated using the polymerase chain reaction, PCR, or alternatively, inserted into a cassette vector, as disclosed in U.S. Pat. No. 5,079,336, the disclosures of which is hereby incorporated by reference.

Expression vectors, host cells and cell cultures suitable for use in the invention are chosen from expression systems capable of synthesizing α-1-antichymotrypsin analogue products. Host cells suitable for use in the invention include prokaryotic and eukaryotic cells that can be transformed to stably contain and express α-1-antichymotrypsin, as disclosed in U.S. Pat. No. 5,079,336, incorporated herein by reference. Suitable types of cells for practicing the present invention include bacterial, yeast and mammalian cells.

Nucleic acids coding for recombinant α-1-antichymotrypsin may be expressed in prokaryotic or eukaryotic host cells, including the most commonly used bacterial host cell for the production of recombinant proteins, *E. coli*. Other microbial strains may also be used, such as *Bacillus subtilis* and other enterobacteriaceae such as *Salmonella typhimurium* or *Serratia marcescens*, various species of Pseudomonas or other bacterial strains.

Commonly used eukaryotic systems include yeast, such as *Saccharomyces cerevisiae*, insect cells such as *Spodoptera frugiperda*, chicken cells such as E3C/O and SL-29, mammalian cells such as HeLa, Chinese hamster ovary cells (CHO), COS-7 or MDCK cells, and the like. The foregoing list is illustrative only and is not intended in any way to limit the types of host cells suitable for expression of the nucleic acid sequences of the invention.

As used herein, expression vectors refer to any type of vector that can be manipulated to contain a nucleic acid sequence coding for recombinant α-1-antichymotrypsin, such as plasmid expression vectors and viral vectors. The selection of the expression vector is based on compatibility with the desired host cell such that expression of the nucleic acid coding for recombinant α-1-antichymotrypsin results. Plasmid expression vectors comprise a nucleic acid sequence of the invention operably linked with at least one expression control element such as a promoter. In general, plasmid vectors contain replicon and control sequences derived from species compatible with the host cell. To facilitate selection of plasmids containing nucleic acid sequences of the invention, plasmid vectors may also contain a selectable marker such as a gene coding for antibiotic resistance. Suitable examples include, and are not limited to, the genes coding for ampicillin, tetracycline, chloramphenicol or kanamycin resistance.

Suitable expression vectors, promoters, enhancers and other expression control elements are known in the art and may be found in Sambrook et al., *Molecular Cloning: A Laboratory Manual*, second edition, Cold Spring Harbor Laboratory Press, Cold Spring Harbor, N.Y. (1989). The plasmids and vectors set forth below are examples only and are not meant to be limiting in any way. Plasmids such as pBR322, pUC18, pUC19, pZMS, and pZM may be used for expression in *E. coli*. Plasmid YRp7 may be used for expression in *S. cervisiae*. Plasmids such as pMT2 and pMSG may be used for expression in mammals. Suitable vital vectors include baculovirus, Vaccinia virus and adenovirus.

The particulars for the construction of expression systems suitable for desired hosts are known to those in the art. For recombinant production of the protein, the DNA encoding it is suitably ligated into the expression system of choice and the system is then transformed into the compatible host cell which is then cultured and maintained under conditions wherein expression of the foreign gene takes place. The peptide of this invention is then recovered from the culture, either by lysing the cells or from the culture medium as appropriate and known to those in the art.

Specifically, the expression vector comprising the nucleic acid sequence coding for human α-1-antichymotrypsin preferably further comprises transcription and translation control elements operatively linked to the nucleic acid sequence coding for human α-1-antichymotrypsin. For example, in an upstream position may be a promoter followed by a translation initiation signal comprising a ribosome binding site and an initiation codon, and in a downstream position may be a transcription termination signal. The transcription and translation control elements may be ligated in any functional combination or order. The transcription and translation control elements used in any particular embodiment of the invention will be chosen with reference to the type of cell into which the expression vector will be introduced, so that an expression system is created.

It is preferable to use a strong promoter, such as the *E. coli* trp-lac promoter or the T7 pL promoter, to ensure high levels of expression of the protein product. The plNomp and β-lactamase promoters have been found to give low or no yields of α-1-antichymotrypsin when operatively linked with DNA coding for α-1-antichymotrypsin. It is also preferable that the promoter is an inducible promoter, such as $P_L$ promoter, to avoid possible host cell toxicity during accumulation of the product.

Alternatively, a gene expression system based on bacteriophage T7 RNA polymerase as disclosed in Studier and Moffatt, *J. Mol. Biol.*, 1986, 189, 113, which is specifically incorporated as if fully set forth herein, may be used. In this system, *E. coli* cells transformed with plasmids containing the bacteriophage T7 promoter operatively linked with a DNA sequence coding for a selected product are infected with lambda phage having an expressible gene for T7 RNA polymerase. The cells are infected with phage after sufficient copies of the plasmids are present in the host cells and protein synthesis begins soon after infection.

Transformed host cells containing a DNA sequence coding for human α-1-antichymotrypsin analogues may then be grown in an appropriate medium for the host. Where an inducible promoter is employed, the host cell may be grown to high density and the promoter turned on for expression of the fusion protein and protease. Where the promoter is not inducible, then constitutive production of the protein product will occur. Constitutive production of the α-1-antichymotrypsin analogue is preferable in expressions systems where it is not substantially toxic to the host cell. The cells may be grown until there is no further increase in analogue formation or the ratio of nutrient consumption to analogue formation falls below a predetermined level, at which time the cells may be harvested, lysed and the protein product obtained and substantially purified in accordance with conventional techniques. Such techniques include chromatography, electrophoresis, extraction, and density gradient centrifugation.

As used herein, host cells transformed with an appropriate expression vector, and cell cultures of such host cells may be used to synthesize α-1-antichymotrypsin of the present invention. Protein preparations of recombinant analogues of α-1-antichymotrypsin may also be prepared from host cells and cell cultures.

Host cells are cultured in medium appropriate to maintain the cells and produce a mixture of cells and medium containing recombinant α-1-antichymotrypsin analogues. Alternatively, the mixture may be purified such that recombinant α-1-antichymotrypsin is purified therefrom.

Purification methods useful herein include, but are not limited to, ion exchange chromatography, affinity chromatography, electrophoresis, dialysis and other methods of protein purification known in the art. Protein preparations, of purified or unpurified recombinant α-1-antichymotrypsin analogue produced by host cells, are produced which comprise α-1-antichymotrypsin and perhaps other material from the mixture of cells and medium, depending on the degree of purification of the protein.

Thus, the present invention provides a method of producing human α-1-antichymotrypsin or analogue comprising culturing a host cell capable of expressing human α-1-antichymotrypsin or analogue to produce cells containing human α-1-antichymotrypsin or analogue and optionally purifying the mixture to produce human α-1-antichymotrypsin or analogue in a purified form.

Protein preparations, of purified or unpurified recombinant α-1-antichymotrypsin analogue produced by host cells, are accordingly produced which comprise α-1-antichymotrypsin and other material such as host cell components and/or cell medium, depending on the degree of purification of the protein.

The term "purified", when used to describe the state of nucleic acid sequences of the invention, refers to nucleic acid sequences substantially free of nucleic acid not coding for human α-1-antichymotrypsin or other materials normally associated with nucleic acid in non-recombinant cells, i.e., in its "native state".

The term "purified" or "in purified form" when used to describe the state of α-1-antichymotrypsin protein or analogue protein, refers to α-1-antichymotrypsin or analogue free, to at least some degree, of cellular material or other material normally associated with it in its native state. Preferably α-1-antichymotrypsin or analogue has a purity (homogeneity) of at least about 25% to about 100%. More preferably the purity is at least about 50%.

The analogues of α-1-antichymotrypsin of the present invention exhibit antichymotrypsin activity and are useful in the same manner as native or wild-type α-1-antichymotrypsin. The analogues are useful as chymase inhibitors, and in the treatment and prevention of blood clots, reperfusion injury, and inflammation of the lungs. In the case of lung inflammation, inflammation may be caused by aspiration of an acidic substance such as and not limited to stomach contents, smoke, infection, such as pathogen infection including infection from a gram negative bacterium (Escherichia and Pseudomonas, for example).

The analogues of the invention may be administered with a pharmaceutically-acceptable carrier or diluent, such as a saline solution or other buffer. Suitable pharmaceutical carriers are well known in the art and are described for example, in Gennaro, Alfonso, ed., Remington's Pharmaceutical Sciences, 18th Edition, 1990, Mack Publishing Co., Easton Pa., a standard reference text in this field. Carriers may be selected with regard to the intended route of administration and the standard pharmaceutical practice. Dosages will be set with regard to weight, and clinical condition of the patient. The proportional ratio of active ingredient to carrier will naturally depend on the chemical nature, solubility, and stability of the analogues, as well as the dosage contemplated.

The analogues of the invention may be employed in the method of the invention singly or in combination with other compounds, including and not limited to other analogues of the invention. The method of the invention may also be used in conjunction with other treatments including and not limited to antibodies, toxins, and antisense oligonucleotides. For in vivo applications the amount to be administered will also depend on such factors as the age, weight, and clinical condition of the patient. The analogues of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the analogues, medicaments, and compositions of the present invention, may determine the sites in the organism to which the analogue may be delivered. For instance, topical application may be administered in creams, ointments, gels, oils, emulsions, pastes, lotions, and the like. For parenteral administration, the analogues may be used in the form of a sterile aqueous solution which may contain other solute, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added.

Methods of inhibiting chymase, treating skin inflammation, treating and preventing blood clotting, treating lung inflammation, and treating reperfusion injury are also provided whereby an α-1-antichymotrypsin analogue having amino acid substitutions at position 358, or positions 356–361 with position 358 selected from the amino acids identified above; or wherein the amino acids of human wild type α-1-antichymotrypsin Thr-Leu-Leu-Ser-Ala-Leu corresponding to positions 356–361 are substituted with Ile-Pro-Xxx-Ser-Ile-Pro-; is added to a sample exhibiting the condition to be treated.

For purposes of the current invention, animals include but are not limited to the Order Rodentia, such as mice and the Order Logomorpha, such as rabbits; more particularly the Order Carnivora, including Felines (cats) and Canines (dogs); even more particularly the Order Artiodactyla, Bovines (cows) and Suines (pigs) and the Order Perissodactyla, including Equines (horses); and most particularly the Order Primates, Ceboids and Simoids (monkeys) and Anthropoids (humans and apes). The animals of the most preferred embodiments are humans.

EXAMPLES

PRODUCTION AND PURIFICATION OF RECOMBINANT α-1-ANTICHYMOTRYPSIN ANALOGUES

Materials

Chymotrypsin was obtained from Sigma or Boehringer-Mannheim. All chromophoric protease substrates were obtained from Bachem, as was phenylmethylsulfonyl fluoride (PMSF).

Human serum α-1-antichymotrypsin was prepared using a procedure based on the work of Tsuda et al., Tokai, *J. Exp. Clin. Med.*, 1982, 7, 201. This method affords pure α-1-antichymotrypsin in three steps, batchwise elution from DNA cellulose, G-150 chromatography and KCl gradient elution from DNA cellulose.

Plasmid constructions and DNA manipulations were carried out following Sambrook et al., *Molecular Cloning: A Laboratory Manual*, second edition, Cold Spring Harbor Laboratory Press, Cold Spring Harbor, N.Y. (1989).

Identification and Sequencing of the Gene from Human Antichymotrypsin

A human liver cDNA library in the phage expression vector lambda-gt11 provided by Mitchell Weiss, Department of Human Genetics, University of Pennsylvania, was screened according to the method of Young and Davis, *Proc. Natl. Acad. Sci., U.S.A.*, 1977, 74, 5463, with polyclonal antisera raised against C1 esterase inhibitor (DAKO, Santa Barbara, Calif.), a related serine protease inhibitor. Positives clones were picked, rescreened and plaque-purified. DNA sequencing was performed with the chain termination method of Sanger et al., *Proc. Natl. Acad. Sci.*, 1977, 74, 5463, using oligonucleotide primers obtained from the Nucleic Acid Synthesis Center of the Wistar Institute (Philadelphia, Pa.).

The DNA sequence and the derived amino acid sequence of the EcoR1 fragment from one of the positive lambda-gt11 cDNA clones contained the entire coding region of the mature human α-1-antichymotrypsin, as depicted in FIG. 1. The construct also included a 21 nucleotide extension of the 5'-end encoding 7 amino acids, comprising the sequence 5'-Met-Ala-Ser-Leu-Cys-His-Pro- (SEQ ID NO: 5). The mature protein contains 398 amino acids ($M_r$ 45,031) starting from amino acid position 1, Asn, at the amino terminus and contains a single cysteine residue at position 236.

Preparation of Recombinant α-1-Antichymotrypsin and Analogues Having Tryptophan at Amino Acid Position 358

The nucleic acid sequence coding for human α-1-antichymotrypsin may be obtained as described above and subcloned into pUC19 (Promega, Madison, Wis.) as set forth in U.S. Pat. No. 5,079,336, incorporated herein by reference. In the present example, however, the analogue of α-1-antichymotrypsin having the substitution of tryptophan for leucine at position 358, rACT-L358W, was prepared according to PCR as follows.

The commercially available plasmid pKC30 was cut by BamHI, the single strand created staggered ends which were filled by Klenow reaction. The linearized plasmid with both ends blunt ended was self ligated, and *E. coli* N4830-1 was transformed by the ligation reaction mixture. The plasmid purified from transformants was pKC30(-BamHI), indicating pKC30 with the only BamHI site removed. This pKC30 (-BamHI) was digested by HpaI, and created two blunt ends for the next ligation step.

A 0.2 kb fragment containing a ribosome binding site was cut out of the following set of plasmids: pAR 3038, pAR3039, and pAR3040, by XbaI and EcoRV. The EcoRV cut created a blunt end. The staggered end created by XbaI was filled by the Klenow reaction. With both ends blunted, the three 0.2 kb fragments were separately ligated to HpaI digested pKC30(-BamHI). The three ligation mixtures were used to transform N4830-1 separately. Three vectors were obtained from these transformants. They were named pZM3038, pZM3039, and pZM3040, corresponding to three reading frames. These pZM vectors contained a pL promoter from pKC30, and received Shine-Dalgarno sequences from pAR vectors. The unique cloning site of these vectors is BamHI which is located in the fragment from pAR.

One of pZM3038, pZM3039, or pZM3040 was cut by NheI, and produced two fragments, about 5.9 kb, and about 0.75 kb. The 5.9 kb fragment was gel purified and ligated to recircularize. N4830-1 was transformed with this ligation reaction. The plasmid isolated from the transformants was named pZMs. pZMs has a unique cloning site—NheI which is downstream from the pL promoter, Shine-Dalgarno sequence, and the start codon.

Primers 1, 2, 3, and 4, as shown in Table 1, were prepared by standard techniques set forth in Sambrook et al., *Molecular Cloning: A Laboratory Manual*, second edition, Cold Spring Harbor Laboratory Press, Cold Spring Harbor, N.Y.

(1989) and used in a polymerase chain reaction (PCR) protocol to introduce bases coding for tryptophan into the sequence coding for α-1-antichymotrypsin. Standard PCR protocols are known to those skilled in the art.

TABLE 1

| Primer | Sequence | SEQ ID NO: |
|---|---|---|
| 1 | 5'-CCCCATATGGCTAGCAACAGCCCACTTG-3' | 1 |
| 2 | 5'-TAATGCAGACCAGAGGGTGA-3' | 2 |
| 3 | 5'-ATCACCCTCTGGTCTGCATTA-3' | 3 |
| 4 | 5'-TTTCATATGGCTAGCGCTCTAGGCTTGC-3' | 4 |

The full-length nucleotide sequence was created in two parts, Fragments A and B, which were combined to produce the full-length nucleotide sequence.

To construct Fragment A, two primers were used. Primer 1 contains the 5' sequence of the coding or sense strand for α-1-antichymotrypsin with an extended 5' tail which contains an NheI cloning site, which is shown underlined in Table 1. Primer 2 comprises a 3' tail having bases coding for tryptophan to replace the bases coding for leucine at position 358 (the tryptophan codon is shown in bold letters in Table 1). Primers 1 and 2 were then used with the polymerase chain reaction and the sequence coding for α-1-antichymotrypsin subcloned in pUC19 to produce Fragment A that codes for the N-terminus through position 358.

Standard PCR methods were followed for the production of Fragment A. 1 µl of 100 ng/µl of Primer 1 and 1 µl of 100 ng/µl of Primer 2, 10 µl of 10× PCR buffer, 10 µl of 2 mM dNTP and 0.5 µl of Taq enzyme were added to 10 ng of template DNA, pUC19 containing the α-1-antichymotrypsin gene, with distilled water bringing the reaction volume to 100 µl. Three steps of PCR were performed, 94° C. for 15 seconds, 52° C. for 15 seconds, and 72° C. for 1 second. The three steps equal one cycle, thirty cycles were run.

To construct Fragment B, two different primers were used. Primer 3 contains nucleotides of the coding or sense strand comprising a 3' tail having bases coding for tryptophan to replace the bases coding for leucine at position 358 (the tryptophan codon is shown in bold letters in Table 1). Primer 4 has an extended 5' tail that contains an NheI cloning site, which is shown underlined in Table 1. Primers 3 and 4 were then used with the polymerase chain reaction and the sequence coding for α-1-antichymotrypsin subcloned in pUC19 to produce fragment B that codes for position 358 through the C-terminus. The PCR protocol set forth above for the production of Fragment A was also followed for the production of Fragment B.

The full-length sequence was then produced by the protocol set forth above for Fragment A, with 5–10 ng of each of Fragment A and Fragment B. The fragments were denatured and reannealed. The fragments were reannealed to produce heteroduplexes of Fragments A and B overlapping at a sequence coding for tryptophan that was created via Primers 2 and 3. The heteroduplexes of Fragments A and B were extended using Taq DNA polymerase with the overlapping portions of Fragments A and B serving as primers to produce the full-length sequence coding for α-1-antichymotrypsin having tryptophan substituted for leucine at position 358 of the wild-type. The full-length sequences were then amplified using Primers 1 and 4.

The amplified full-length sequence was then digested with NheI and inserted into the expression vector pZMs, which was digested with NheI. E. coli was then transformed with pZMs containing the full length gene. As such, analogues of α-1-antichymotrypsin with an altered amino acid position 358 of the reactive site were expressed. Thus, leucine at amino acid position 358 was changed to tryptophan. This analogue is represented herein as rACT-L358W. Other analogues of human wild type α-1-antichymotrypsin of the present invention may be similarly prepared.

Preparation of Recombinant α-1-Antichymotrypsin Having Met-Ala-Ser or Ala-Ser N-Terminal Extension Stable monomers were expressed directly by eliminating the N-terminal cysteine residue through deletion of the nucleotides encoding the Leu-Cys-His-Pro (SEQ ID NO: 6) sequence within the N-terminal sequence Met-Ala-Ser-Leu-Cys-His-Pro (SEQ ID NO: 5) encoded within the nucleotide sequence of wild type α-1-antichymotrypsin to produce the nucleotide sequence encoding rMAS-ACT. As such, the amino acids leucine, cysteine, histidine and proline at amino acid positions −4 to −1 of wild type α-1-antichymotrypsin were deleted. The N-terminal extension becomes methionine-alanine-serine at amino acid positions −3 to −1. Such extension was accomplished by PCR amplification, set forth above, of the entire coding sequence with an N-terminal primer 5'-CCCCATATGGCTAGCAACAGCCCACTTG-3' (SEQ ID NO: 1). The C-terminal primer was 5'-TTTCATATGGCTAGCGCTCTAGGCTTGC-3' (SEQ ID NO: 4) in which the underlined sequence GCTAGC served as the insertion site. The underlined CTA sequence creates a TAG termination codon in the sense strand of the vector. The sequence was cloned into pZMs. The amplified full-length sequence was digested with NheI and inserted into the expression vector pZMs, which was digested with Nhe I. E. coli was then transformed with pZMs containing the gene with the altered N-terminal extension. As such, analogues of α-1-antichymotrypsin were produced by altering amino acid positions −4 to −1, such that the amino acids leucine, cysteine, histidine and proline were deleted. This analogue is represented herein as rMAS-ACT.

Expression of rACT Analogues

E. coli N4830-1 was transformed with the expression vectors pACT-L358W, pMAS-ACT, pAS-ACT, pMAS-ACT-L358W or pAS-ACT-L358W by standard calcium chloride methods as described by Sambrook et al., Molecular Cloning: A Laboratory Manual, second edition, Cold Spring Harbor Laboratory Press, Cold Spring Harbor, N.Y. (1989).

Small scale growth conditions and extraction

Fresh overnight cultures of E. coli strain N4830-1 transformed with the aforementioned expression vectors were diluted to 1.5% in LB broth containing ampicillin (Na$^+$ salt, 0.1 mg/ml) and grown at 30° C. in a shaking incubator to an $A_{600nm}$ of 0.18, induced by raising the temperature to 42° C. and grown for an additional five to eight hours. The cells were centrifuged and disrupted in a French press.

Purification and Characterization of Recombinant α-1-Antichymotrypsin Analogues Large-Scale Growth of E. coli E. coli strain N4830-1 transformed with the aforementioned expression vectors were grown in LB media containing ampicillin (Na$^+$ salt, 0.1 m/ml) at 30° C. to an $A_{600nm}$ of 0.18 in a 15 L carboy fitted with an oxygen bubbler. The cells were induced by raising the temperature to 42° C. and grown for an additional six hours to a final $A_{600nm}$ of approximately 0.9–1.0.

Extraction and column chromatography

All purification steps were carried out at 4° C. In a typical preparation of α-1-antichymotrypsin analogue, cell paste was dispersed in 10 mM potassium phosphate buffer, pH 6.9 (25 ml) and lysed by three passes through a French press at 10,000 psi and 4° C. Cell debris was removed by centrifugation at 30,000× g for 30 minutes at 4° C. Supernatant (25 ml) was loaded onto a column (4.9 cm$^2$×37 cm) of Sepharose Fast Q (Pharmacia) that had been equilibrated to 50 mM Tris-Cl, pH 7.5, containing 50 mM KCl. Protein eluted with a linear gradient of KCl in 50 mM Tris-Cl, pH 7.5 (50–500 mM in 2 L). Fractions (15 ml) were monitored for protein by $A_{280nm}$ and assayed for antichymotrypsin activity as described herein. Analogue eluted at approximately 200 mM KCl. Fractions containing analogue were combined and dialyzed against two volumes (2.5 L each) of 10 mM potassium phosphate buffer, pH 6.9 over 48 hours. The dialyzed solution was then applied to a DNA-cellulose column (1.7 cm$^2$×20 cm) that had been pre-equilibrated with 10 mM potassium phosphate, pH 6.9, containing 10 mM KCl. After loading, the column was first washed with the same buffer (20 ml). The column was eluted with a linear gradient of KCl (10–500 mM, 300 ml) in the same buffer. Fractions (8 ml) were assayed for protein and antichymotrypsin activity as described herein. Analogue eluted at approximately 350 mM KCl. Fractions containing antichymotrypsin activity were analyzed for purity by SDS-PAGE, performed according to Laemmli, Nature (London) 1970, 227, 680. Each portion was concentrated by ultrafiltration using Amicon YM-10 membranes and dialyzed overnight against 50 mM Tris-Cl, pH 7.5 (500 ml). In some cases recombinant protein was further purified on an FPLC Mono Q anion exchange column, using the conditions described above.

Antichymotrypsin Activity Assays

Antichymotrypsin activity could not be directly measured in crude bacterial lysates because of large background inhibitory activity in the lysate itself. The background activity was separated from the antichymotrypsin by anion exchange chromatography using a Mono Q HR5/5 anion exchange FPLC column (Pharmacia) fitted into a pump (LKB 2150 pump), a 2152 gradient controller and a UV absorbance detector (Waters 440 UV absorbance detector) with an extended wavelength module. Chromatography was typically conducted on the extract from 200 mg of cells. The separation involved an isocratic wash (5 minutes) with 50 mM Tris-Cl buffer, pH 7.5, containing 50 mM KCl, followed by a linear gradient of KCl (50–350 mM in 30 minutes) at a flow rate of 1.0 ml/minute. Protein absorbance was monitored at both 214 and 280 nm. Fractions (1.0 ml) were collected and assayed for antichymotrypsin or antitrypsin activity measured as the inhibition of the chymotrypsin-catalyzed hydrolysis of substrate N-suc-Ala-Ala-Pro-Phe-p-nitroanilide (0.1 ml of 10 mM solution in 90% DMSO), DelMar et al., Anal. Biochem., 1979, 99,316 or of trypsin-catalyzed hydrolysis of substrate N-Bzl-Pro-Phe-Arg-p-nitroanilide (0.02 ml of a 14.6 mM solution in 90% DMSO). A typical chymotrypsin assay contained in (1.0 ml): 100 mM Tris-Cl buffer, pH 8.3, 0.005% (v/v) Triton X-100, bovine pancreatic chymotrypsin (18 mmol) and column eluate (0.005–0.5 ml). The assay mixture was pre-incubated at room temperature for 5 minutes, substrate (0.01 ml of a 10 mM solution in 90% DMSO) was added, and remaining chymotrypsin activity was determined by the rate of change in $A_{410nm}$ caused by the release of p-nitroaniline. A typical trypsin assay contained (in 1.0 ml); 100 mM Tris-Cl buffer, pH 8.3, 0.005% (v/v) Triton X-100, bovine trypsin (8.6 pmol) and sample (0.005–0.5 ml). The assay mixture was preincubated at room temperature for 10 minutes before substrate (0.02 ml of a 15 mM solution in 90% DMSO) was added and remaining trypsin activity was determined as above. Measurements of optical absorbance were conducted at 25° C. using a spectrophotometer (Hewlett Packard 8452A) fitted with a temperature controlled sample compartment.

INTERACTION OF RECOMBINANT α-1-ANTICHYMOTRYPSIN AND ANALOGUES WITH HUMAN CHYMASE

Materials

Peptide-nitroanilide substrates were purchased from Sigma or Bachem. TSK-Heparin-SPW HPLC column was purchased from Supelco. Heparin-Sepharose was from Pharmacia. Immobilon-P (PVDF membranes) was purchased from Millipore.

The analogue of antichymotrypsin wherein the leucine at position 358 of wild-type is substituted with tryptophan (W) was produced as described herein.

Purification of Human Chymase

Mast cell proteinases were extracted from human skin and fractionated on a 500 ml heparin-Sepharose column. Chymase, eluted from heparin-Sepharose in single step with 2M NaCl, 0.1M MOPS (pH 6.8) was further purified by affinity chromatography using soybean trypsin inhibitor (SBTI)-Sepharose. The fraction of chymase binding to heparin-Sepharose was variable. In extracts resulting in an enzyme heparin-Sepharose binding of 30–70%, an alternate purification method was used. Chymase in the flow-through was precipitated by addition of protamine chloride. After solubilization of the precipitate in high salt buffer, chymase was absorbed to a phenylbutylamine-Sepharose column (20 ml resin) and chymase was eluted in a single step by addition of 0.4M NaCl, 0.01M [3-(N-morpholino)-propanesulfonic acid], MOPS, (pH 6.8), 0.2M D tryptophan methyl ester, D-Trp-OMe, solution. The proteinase was then applied to a heparin-Sepharose column where it absorbed to the column and was eluted with a salt gradient.

Chymase purified by both procedures had identical catalytic properties, migrated identically on SDS gels, and had the same stoichiometry of inhibition when titrated against serum ACT. Enzyme purified by both procedures was used in these studies.

Determination of Inhibitor and Proteinase Concentrations

Concentrations of α-1-recombinant antichymotrypsins were determined by titration with chymotrypsin. Titrations were performed in 50 μl (25° C.) containing in 0.1M Tris-HCl, 0.5M NaCl, 0.01% Triton X-100 and 150–300 μM proteinase. Residual activity was determined after 10–15 minute incubations by diluting sample with 1 ml assay buffer containing the substrates SucAAPF-pNA or CBZ-GPA-pNA (carbobenzoxy-Gly-Pro-Arg p-nitroanilide) at 1 mM. Stock chymotrypsin solution was standardized with the active site titrants N-trans-cinnamoylimidazole. Chymase concentrations were determined using its specific activity 2.7 μmol of product min-1/nmol chymase measured under standard assay conditions containing 1 mM of substrate SucAAPF-pNA; $\epsilon_{410}$=8800 (the extinction coefficient of p-nitroaniline) was used to quantify released p-nitroanaline.

Chymase Assay

Reactions of chymase with recombinant α-1-antichymotrypsin and analogues were performed at 25° C. in 50–150 μl of a solution containing 0.2M Tris-HCl (pH 8.0), 1M NaCl, 0.01% Triton X-100 and 150–400 nM chymase. After incubation with inhibitor, independently including the aforementioned analogues, for appropriate times, residual activity was measured by dilution of a sample aliquot in 1 ml assay buffer containing 1 mM substrate as described above. The reactions of chymase with inhibitor were stopped by the addition of a general serine proteinase inhibitor (PMSF) and a sample of the reaction mixture was electrophoresed to determine reaction products.

Reaction of Chymase with Variant rACTs

Stoichiometry of inhibition (SI) values and second order rate constants were determined for the analogues. Titrations (pH 8.0, 1M NaCl, 25° C.) to obtain the SI for each recombinant α-1-antichymotrypsin are presented in FIG. 2. Residual activities in these studies were achieved within minutes and remained constant for at least 24 hours. Second order rate constants ($k_{obs/I}$) were evaluated for all rACTS at (rACT)$_o$/(chymase)$_o$>>1. The reaction of chymase with serum α-1-antichymotrypsin, reactions appears pseudo first order when (I)$_o$/(E)$_o$ ratios are approximately 10 fold higher than the SI. Reaction conditions in rate studies were similar to titrations, measurements were made at NaCl concentrations of 1M and 2M.

Inhibition Rate Constants

Progress curves were determined under pseudo-first order conditions ((I)$_o$>>(E)$_o$) in the presence of substrate. Reactions contained 0.25 to 1.0 mM SucAAPF-pNA, 2–2.5 nM chymase and inhibitor. Absorbance was continually monitored for 15 minutes, and instantaneous velocities were determined over 1 minute intervals by regression analysis. Plots of the instantaneous velocity vs time (t) were fit by non-linear methods to the expression $Ae^{-k't}$ to determine k', the apparent first order rate constant; (A) is the initial activity. $k_{obs/I}$ was calculated from the relationship, $k_{obs/I}$= k'((S/Km)+1)/I, where S is the initial substrate concentration, Km is the Michaelis constant for chymase hydrolysis of the substrate under the experimental conditions, and I is the initial inhibitor concentration. Reactions were monitored for at least three half-lives. Km was 0.80 mM in 1.0 M NaCl and 0.49 in 2.0M NaCl.

Rate constants and SI for all variants are collected in Table 2. Only minor changes in values were observed at the two different NaCl concentrations. The results illustrate the importance of the P1 residue, change of Leu to Trp, in modulating the SI and rate of inhibition. The reaction of chymase with serum ACT has a stoichiometry of inhibition (SI) of 4.0 due to generation of degraded inhibitor (3.5 moles degraded inhibitor/mole chymase) in a reaction competing with chymase inhibition.

TABLE 2

Kinetic Parameters for the Reaction of Human Chymase with Recombinant α-1-Antichymotrypsin and Analogues

| rACT variant | NaCl (M) | $k_{obs}/I^a$ ($M^{-1} S^{-1}$) | SI |
| --- | --- | --- | --- |
| Leu358W | 1 | 151,00 | 1.5 |
| Leu358W | 2 | 280,000 | 1.2 |
| Leu358 | 1 | 27,000 | 4.0 |
| Leu358 | 2 | 42,500 | 3.5 |
| Leu358 (Cas) | 1 | 60,000 | 2.0 |

$^a$experimental conditions for measurement rate constants were similar to those of titrations except for presence of substrate and 9% Me$_2$SO$_4$. Most $k_{obs}/[I]$ values are the average of two experiments and deviation from the average was typically less than 15%. $K_{obs}/[I]$ values for rACT-L358 in 2 M NaCl and rACT-L258W in 1 M NaCl were based on 4 and 5 measurements, respectively; SD were 8% and 15% of the reported values respectively. Leu358 (Cas) refers to the cassette version of the analogue prepared according to the methods set forth in U.S. Pat. No. 5,079,336.

Various modifications of the invention in addition to those shown and described herein will be apparent to those skilled in the art from the foregoing description. Such modifications are also intended to fall within the scope of the appended claims.

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
      ( A ) LENGTH: 28
      ( B ) TYPE: Nucleic Acid
      ( C ) STRANDEDNESS: Single
      ( D ) TOPOLOGY: Linear ( i v ) ANTI-SENSE: NO ( x i ) SEQUENCE DESCRIPTION: SEQ ID NO: 1:

CCCCATATGG CTAGCAACAG CCCACTTG  28

( 2 ) INFORMATION FOR SEQ ID NO: 2:

( i ) SEQUENCE CHARACTERISTICS:
      ( A ) LENGTH: 20
      ( B ) TYPE: Nucleic Acid
      ( C ) STRANDEDNESS: Single
      ( D ) TOPOLOGY: Linear ( i v ) ANTI-SENSE: NO ( x i ) SEQUENCE DESCRIPTION: SEQ ID NO: 2:

TAATGCAGAC CAGAGGGTGA  20

( 2 ) INFORMATION FOR SEQ ID NO: 3:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: NO ( x i ) SEQUENCE DESCRIPTION: SEQ ID NO: 3:

ATCACCCTCT GGTCTGCATT A                                                                                                 21

( 2 ) INFORMATION FOR SEQ ID NO: 4:

( i ) SEQUENCE CHARACTERISTICS:
        ( A ) LENGTH: 28
        ( B ) TYPE: Nucleic Acid
        ( C ) STRANDEDNESS: Single
        ( D ) TOPOLOGY: Linear ( i v ) ANTI-SENSE: NO ( x i ) SEQUENCE DESCRIPTION: SEQ ID NO: 4:

TTTCATATGG CTAGCGCTCT AGGCTTGC                                                                     28

( 2 ) INFORMATION FOR SEQ ID NO: 5:

( i ) SEQUENCE CHARACTERISTICS:
        ( A ) LENGTH: 7
        ( B ) TYPE: Amino Acid
        ( D ) TOPOLOGY: Linear ( x i ) SEQUENCE DESCRIPTION: SEQ ID NO: 5:

MET ALA SER LEU CYS HIS PRO
1                   5

( 2 ) INFORMATION FOR SEQ ID NO: 6:

( i ) SEQUENCE CHARACTERISTICS:
        ( A ) LENGTH: 4
        ( B ) TYPE: Amino Acid
        ( D ) TOPOLOGY: Linear ( x i ) SEQUENCE DESCRIPTION: SEQ ID NO: 6:

LEU CYS HIS PRO
1

( 2 ) INFORMATION FOR SEQ ID NO: 7:

( i ) SEQUENCE CHARACTERISTICS:
        ( A ) LENGTH: 6
        ( B ) TYPE: Amino Acid
        ( D ) TOPOLOGY: Linear ( x i ) SEQUENCE DESCRIPTION: SEQ ID NO: 7:

THR LEU LEU SER ALA LEU
1                 5

( 2 ) INFORMATION FOR SEQ ID NO: 8:

( i ) SEQUENCE CHARACTERISTICS:
        ( A ) LENGTH: 6

( B ) TYPE: Amino Acid
( D ) TOPOLOGY: Linear ( x i ) SEQUENCE DESCRIPTION: SEQ ID NO: 8:

ILE PRO XAA SER ILE PRO
1               5

What is claimed:

1. An analogue of human wild type α-1-antichymotrypsin wherein only the amino acid corresponding to the leucine at amino acid position 358 of wild-type α-1-antichymotrypsin is substituted with an amino acid selected from the group consisting of tryptophan and phenylalanine.

2. An analogue of human wild type α-1-antichymotrypsin wherein the amino acids corresponding to the amino acids Thr-Leu-Leu-Ser-Ala-Leu at positions 356 to 361 of wild-type α-1-antichymotrypsin are substituted with amino acids Ile-Pro-Xxx-Ser-Ile-Pro, wherein Xxx is selected from the group consisting of methionine, tryptophan and phenylalanine.

3. An analogue of claim 2 wherein the amino acid at Xxx is methionine.

4. An analogue of claims 1, 2, or 3 having chymase inhibiting activity.

5. An analogue of claims 1, 2, or 3 optionally comprising an N-terminal extension selected from the group consisting of methionine-alanine-serine and alanine-serine.

6. An analogue of claim 1 wherein the nucleotides coding for leucine at amino acid position 358 have been substituted with nucleotides coding for tryptophan.

7. A purified nucleic acid sequence coding for an analogue of human wild type α-1-antichymotrypsin wherein only the amino acid corresponding to the leucine at amino acid position 358 of human wild-type α-1-antichymotrypsin is substituted with an amino acid selected from the group consisting of tryptophan and phenylalanine.

8. A purified nucleic acid sequence of an analogue of human wild type α-1-antichymotrypsin wherein nucleic acids coding the amino acids corresponding to the amino acids Thr-Leu-Leu-Ser-Ala-Leu at positions 356 to 361 of wild-type α-1-antichymotrypsin are substituted with nucleic acids coding for amino acids Ile-Pro-Xxx-Ser-Ile-Pro, wherein Xxx is selected from the group consisting of methionine, tryptophan and phenylalanine.

9. The purified nucleic acid sequence of claim 8 wherein the amino acid Xxx is methionine.

10. The purified nucleic acid sequence of claims 7, 8, or 9 optionally having an N-terminal extension selected from the group consisting of methionine-serine-alanine and alanine-serine.

11. An expression vector comprising a nucleic acid sequence encoding the analogue of claim 1.

12. An expression vector comprising a nucleic acid sequence encoding the analogue of claim 2.

13. An expression vector comprising a nucleic acid sequence encoding the analogue of claim 3.

14. A host cell capable of expressing a nucleic acid sequence encoding the analogue of claim 1.

15. A host cell capable of expressing a nucleic acid sequence encoding the analogue of claim 2.

16. A host cell capable of expressing a nucleic acid sequence encoding the analogue of claim 3.

17. A protein preparation comprising the analogue of human α-1-antichymotrypsin of claim 1.

18. A protein preparation comprising the analogue of human α-1-antichymotrypsin of claim 2.

19. A protein preparation comprising the analogue of human α-1-antichymotrypsin of claim 3.

20. A composition comprising an analogue of human wild type α-1-antichymotrypsin in a pharmaceutically acceptable carrier, said analogue having only the amino acid corresponding to the leucine at amino acid position 358 of wild type α-1-antichymotrypsin substituted with an amino acid selected from the group consisting of tryptophan and phenylalanine.

21. A composition comprising an analogue of human wild type α-1-antichymotrypsin and a pharmaceutically acceptable carrier, said analogue having the amino acids corresponding to the amino acids Thr-Leu-Leu-Ser-Ala-Leu at positions 356 to 361 of wild-type α-1-antichymotrypsin are substituted with amino acids Ile-Pro-Xxx-Ser-Ile-Pro, wherein Xxx is selected from the group consisting of tryptophan, methionine and phenylalanine.

22. The composition of claim 21 wherein the amino acid Xxx is methionine.

23. The composition of claim 20 for the treatment of reperfusion injury.

24. The composition of claim 20 for the treatment of inflammation of the lung.

25. The composition of claim 20 for the inhibition of chymase.

26. The composition of claim 20 wherein said amino acid substituted is tryptophan.

27. The composition of claim 20 wherein said amino acid substituted is phenylalanine.

28. The composition of claim 21 for the inhibition of chymase.

29. The composition of claim 21 for treating inflammation of the lung.

30. A cell culture capable of expressing an analogue of human wild type α-1-antichymotrypsin obtained by transforming cells with an expression vector comprising a nucleic acid sequence wherein only the amino acid corresponding to the leucine at amino acid position 358 of wild-type α-1-antichymotrypsin is substituted with an amino acid selected from the group consisting of tryptophan and phenylalanine.

31. A cell culture capable of expressing an analogue of human wild type α-1-antichymotrypsin obtained by transforming cells with an expression vector comprising a nucleic acid sequence encoding an analogue of alpha-1-antichymotrypsin wherein the amino acids corresponding to Thr-Leu-Leu-Ser-Ala-Leu at positions 356 to 361 of wild-type α-1-antichymotrypsin are substituted with amino acids Ile-Pro-Xxx-Ser-Ile-Pro, Xxx being selected from the group consisting of tryptophan, methionine and phenylalanine.

* * * * *

UNITED STATES PATENT AND TRADEMARK OFFICE
CERTIFICATE OF CORRECTION

Page 1 of 2

PATENT NO. : 5,723,316

DATED : March 3, 1998

INVENTOR(S) : Cooperman et al.

It is certified that error appears in the above-indentified patent and that said Letters Patent is hereby corrected as shown below:

At col. 1, line 35, please delete "serine" and insert therefor --serine--.

At col. 1, line 35, please delete "proteinase" and insert therefor --proteinase--.

At col. 1, line 35, please delete "inhibitor" and insert therefor --inhibitor--.

At col. 6, line 51, please delete "vital" and insert therefor --viral--.

At col. 10, line 20, please delete "Ash" and insert therefor --Asn--.

At col. 11, line 10, please delete "5'-TAATGCAGACCAGAGGGTGA-3'" and insert therefor --5'-TAATGCAGACCAGAGGGTGA-3'--.

At col. 11, line 11, please delete "5'-ATCACCCTCTGGTCTGCATTA-3'" and insert therefor --5'-ATCACCCTCTGGTCTGCATTA-3'--.

At col. 12, line 24, please delete "5'-TTTCATATGGCTAGCGCTCTAGGCTTGC-3'" and insert therefor --5'-TTTCATATG<u>GCTAGC</u>GCT<u>CTA</u>GGCTTGC-3'--.

At col. 12, line 25, please delete "GCTAGC" and insert therefor --<u>GCTAGC</u>--.

At col. 12, line 26, please delete "CTA" and insert therefor --<u>CTA</u>--.

At col. 14, line 10, please delete "Bachcm" and insert therefor --Bachem--.

UNITED STATES PATENT AND TRADEMARK OFFICE
CERTIFICATE OF CORRECTION

PATENT NO. : 5,723,316

DATED : March 3, 1998

INVENTOR(S) : Cooperman et al.

It is certified that error appears in the above-indentified patent and that said Letters Patent is hereby corrected as shown below:

At col. 16, Table 2, please delete "$(M^1S^{-1})$" and insert therefor --$(M^{-1}S^{-1})$--.

At col. 16, line 24, please delete "typicaiiy" and insert therefor --typically--.

Signed and Sealed this

Twenty-third Day of June, 1998

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,723,316

DATED : March 3, 1998

INVENTOR(S) :
        Cooperman et al.

It is certified that error appears in the above-indentified patent and that said Letters Patent is hereby corrected as shown below:

On the Title page, under the Notice : please delete "5,613,194" and insert therefor --5,612,194--.

Signed and Sealed this

First Day of September, 1998

*Attest:*

BRUCE LEHMAN

*Attesting Officer*      *Commissioner of Patents and Trademarks*